United States Patent
Kazmi et al.

(10) Patent No.: US 11,219,605 B1
(45) Date of Patent: *Jan. 11, 2022

(54) METAL NANOPARTICLE MEDICINE WITH A MIXTURE OF NATURAL LIGANDS

(71) Applicant: King Abdulaziz University, Jeddah (SA)

(72) Inventors: Imran Kazmi, Jeddah (SA); Syed Sarim Imam, Riyadh (SA); Muhammad Afzal, Sakaka (SA); Muhammad Shahid Nadeem, Jeddah (SA); Fahad A. Al-Abbasi, Jeddah (SA); Firoz Anwar, Jeddah (SA)

(73) Assignee: King Abdulaziz University, Jeddah (SA)

( * ) Notice: Subject to any disclaimer, the term of this patent is extended or adjusted under 35 U.S.C. 154(b) by 0 days.

This patent is subject to a terminal disclaimer.

(21) Appl. No.: 17/407,860

(22) Filed: Aug. 20, 2021

Related U.S. Application Data

(63) Continuation of application No. 17/314,150, filed on May 7, 2021, now Pat. No. 11,129,797.

(51) Int. Cl.
*A61K 9/51* (2006.01)
*A61K 31/12* (2006.01)
*A61K 31/353* (2006.01)

(52) U.S. Cl.
CPC .......... *A61K 9/5115* (2013.01); *A61K 9/5123* (2013.01); *A61K 9/5192* (2013.01); *A61K 31/12* (2013.01); *A61K 31/353* (2013.01)

(58) Field of Classification Search
CPC .. A61K 9/5115; A61K 9/5123; A61K 9/5192; A61K 31/12; A61K 31/353
See application file for complete search history.

(56) References Cited

U.S. PATENT DOCUMENTS

| | | | |
|---|---|---|---|
| 9,815,701 | B1 | 11/2017 | Awad et al. |
| 10,052,302 | B2 | 8/2018 | Awad et al. |
| 2010/0092535 | A1 | 4/2010 | Cook et al. |
| 2016/0089443 | A1 | 3/2016 | Hu et al. |

FOREIGN PATENT DOCUMENTS

| | | |
|---|---|---|
| CN | 106806949 A | 6/2017 |
| CN | 110128784 A | 8/2019 |

OTHER PUBLICATIONS

Javed etal, Journal of Nanobiotechnology, 18 article No. 172. (Year: 2020).*
Kobayashi et al, Polymer Journal, 4, 460-468. (Year: 2014).*
Guerin et al, Materials, 11, 1154. (Year: 2018).*
Zheng, et al. ; The modulatory effect of nanocomplexes loaded with EGCG Me on intestinal microbiota of high fat diet-induced obesity mice model ; J Food Biochem ; Sep. 26, 2017 ; 8 Pages.
Meena, et al. ; Catechin-loaded Eudragit microparticles for the management of diabetes: formulation, characterization and in vivo evaluation of antidiabetic efficacy ; Journal of Microencapsulation ; Jun. 28, 2017 ; 10 Pages.
Choi, et al. ; Catechin-capped gold nanoparticles: green synthesis, characterization, and catalytic activity toward 4-nitrophenol reduction ; Nanoscale Research Letters 2014, 9; 103 ; 8 Pages.
Wei, et al. ; Phytofabrication of Nanoparticles as Novel Drugs for Anticancer Applications ; Molecules 2019, 24 ; 19 Pages.
Ascar, et al. ; Cytotoxicity and Antioxidant Effect of Ginger Gold Nanoparticles on Thyroid Carcinoma Cells ; J. Pharm. Sci & Res . vol. 11 (3), 2019 ; pp. 1044-1051 ; 8 Pages.
Sayed, et al. ; Ginger Water Reduces Body Weight Gain and Improves Energy Expenditure in Rats, Foods, 9, 38 ; 2020.

* cited by examiner

*Primary Examiner* — Carlos A Azpuru
(74) *Attorney, Agent, or Firm* — Oblon, McClelland, Maier & Neustadt, L.L.P.

(57) ABSTRACT

A nanomedicine for the treatment of obesity comprising either noble metal nanoparticles having surface ligands comprising a mixture comprising (+)-catechin (2R,3S) and gingerol or particles of a carbon nanomaterial having an adsorbed mixture comprising (+)-catechin (2R,3S) and gingerol. Also provided are a method for making the noble metal nanomedicine and the carbon nanomedicine. The nanomedicine is used in a method of treating obesity.

4 Claims, No Drawings

METAL NANOPARTICLE MEDICINE WITH A MIXTURE OF NATURAL LIGANDS

CROSS-REFERENCE TO RELATED APPLICATIONS

The present application is a Continuation of U.S. application Ser. No. 17/314,150, now allowed, having a filing date of May 7, 2021, the entire contents of which is incorporated herein by reference.

BACKGROUND OF THE INVENTION

Field of the Invention

The present disclosure relates to a nanomedicine for the delivery of a phytochemical mixture containing catechin and gingerol by a carrier nanoparticle which may be either a carbon nanomaterial or a noble metal nanoparticle. The nanomedicine is used in a method of treating obesity.

Discussion of the Background

The "background" description provided herein is for the purpose of generally presenting the context of the disclosure. Work of the presently named inventors, to the extent it is described in this background section, as well as aspects of the description which may not otherwise qualify as prior art at the time of filing, are neither expressly nor impliedly admitted as prior art against the present invention.

Obesity is a medical condition in which excess body fat has accumulated to an extent that it may have a negative effect on health. People are generally considered obese when their body mass index (BMI), a measurement obtained by dividing a person's weight by the square of the person's height, is over 30 kg/m$^2$; the range 25-30 kg/m$^2$ is defined as overweight. Obesity increases the likelihood of various diseases and conditions, particularly cardiovascular diseases, type 2 diabetes, obstructive sleep apnea, certain types of cancer, osteoarthritis, and depression [Haslam D. W., and James, W. P., Lancet (Review), 2005, 366, 9492, 1197-1209; and Luppino, F. S., et al., Archives of General Psychiatry, 2010, 63, 3, 220-229].

Obesity is a major health issue in many countries of the world, including the United States of America and Saudi Arabia, and is a cause of or co-morbidity factor for various other disorders or diseases. Obesity is the result of several contributing factors which include genetic and behavioral factors [Hruby, A. and Hu, F. B., Pharmacoeconomics, 2015, 33, 7, 673-689]. Behavioral factors include physical activity, sedentary lifestyle, inactivity, use of medicine, dietary patterns, and environmental exposure to certain harmful substances. Further, cultural and environmental factors such as the availability of inexpensive junk foods, high cost of healthier food options, lack of time and access to facilities for physical activity, skills and education, and food promotion and marketing may also contribute to obesity. A person suffering from obesity in comparison to healthy and normal weight person, may suffer from various serious disorders and health problems, which include hypertension (high blood pressure), mortality (all causes of death), low HDL cholesterol, high LDL cholesterol, dyslipidemia (high levels of triglycerides), stroke, coronary heart disorder, gallbladder disease, type 2 diabetes, a breakdown of cartilage and bone within a joint (osteoarthritis), low life quality, breathing problems and sleep apnea, and various forms of cancers like breast, endometrial, kidney, colon, liver and gallbladder [Meldrum, D. R., et. al., Fertil. Steril., 2017, 107, 4, 833-839; and Bhaskaran, K., et. al., Lancet, 2014, 384, 9945, 755-765].

One common treatment for obesity is through the use of pharmaceuticals. These pharmaceuticals change the physiology of body and act in various modes such as alteration of appetite, reduction in absorption of lipids, and degradation of lipids inside the body [Larder, R., et. al., Proc. Natl. Acad. Sci. USA, 2017, 114, 35, 9421-9426]. The most common anti-obesity drugs include orlistat, lorcaserin, liraglutide, phentermine-topiramate, and naltrexone-bupropion. Each of these drugs, however, is accompanied by a host of side effects like gastrointestinal discomfort or pain, nausea, insomnia, constipation, headaches, and vomiting. For example, orlistat (under brand name Xenical®) was recently approved by the United States-FDA for regular long term intake for the treatment of obesity [US Patent Publication 2009171104A1; and US Patent Publication 20100087520A1]. Orlistat decreases absorption of intestinal fat by inhibition of pancreatic lipase enzyme. Acomplia® (rimonabant), another popular medicine used for the treatment of obesity, works through specific blockade of the endo-cannabinoid receptor system inside the body. Previously Acomplia® was approved for use in Europe for obesity treatment but was not approved by the US FDA because of toxicity and safety issues [Gadde, K. M. et al., Circulation, 2006, 114, 9, 974-984]. In 2008, European Medicines Agency (EMA) recommended the suspension of the rimonabant sale as the toxicity was large in comparison to benefits [Cahill, K. and Ussher, M. H., Cochrane Database Syst Rev., 2011, 3, Article ID CD005353]. Sibutramine (under brand name Meridia®), is also very popular for the treatment of obesity, shows the effect on brain and inhibit activation of the neuronal transmitters, hence decreases hunger. It was also withdrawn from the market of America and Canada in October 2010 because of cardiovascular toxicity [Mead, E., et. al., Cochrane Database Syst Rev., 2016, 11, Article ID CD012436]. The weight loss drugs prescribed in conventional medicine induce many adverse reactions, primarily effecting monoamine neurotransmitters, and causing drug abuse or dependence [Dietrich, M. O., and Horvath, T. L., Nature Reviews Drug Discovery, 2012, 11, 9, 675-691]. For example, sibutramine has been reported to commonly cause adverse events, including dry mouth, insomnia, anorexia, constipation, formation of thrombi, and neurological symptoms [Mead, E., et. al., Cochrane Database of Systematic Reviews, 2016, 29, 11, Article ID CD012436; and Van Der Schoor, C., et al., Ultrastructural Pathology, 2014, 38, 6, 399-405]. Overall, after observing background of all medicines, it is clear that till date, not a single effective medicine is available in market for the proper treatment of obesity.

Another common treatment for obesity is surgery. Surgery is commonly used in morbidly obese patients (BMI 40 kg/m$^2$) or in patients with comorbidities, such as hypertension, diabetes, and obstructive sleep apnea [Kim, J. J., et al., Nutrition in Clinical Practice, 2003, 18, 2, 109-123]. Common surgical complications include infection, postoperative anastomotic fistula, deep vein thrombosis, and long-term complications such as anemia and malnutrition [Ikramuddin, S., et. al., Diabetes Care, 2016, 39, 9, 1510-1518].

Given the dangers of obesity and the shortcomings of available anti-obesity pharmaceuticals, alternative treatments may pose significant improvements for obesity treatment or prevention.

SUMMARY OF THE INVENTION

The present disclosure relates to a noble metal nanomedicine, comprising noble metal nanoparticles comprising a noble metal and having a mean particle size of 5 to 500 nm and a mixture of (+)-catechin (2R,3S) and gingerol bound to a surface of the noble metal nanoparticles, the binding occurring non-oxidatively through non-deprotonated alcohol and ether functional groups and/or physisorption, wherein the mixture has a catechin to gingerol molar ratio of 5:1 to 1:5 and the mixture makes up at least 50 wt % of all ligands bound to the surface of the noble metal nanoparticles, based on a total weight of ligands bound to the surface of the noble metal nanoparticles.

In some embodiments, the noble metal is at least one selected from the group consisting of gold, silver, and platinum.

In some embodiments, the mixture is substantially free of proteins.

In some embodiments, the mixture is substantially free of non-catechin flavonoids.

In some embodiments, the mixture is substantially free of non-(+)-catechin (2R,3S) catechins.

In some embodiments, the mixture is present in an amount of 1 to 50 wt %, based on a total weight of noble metal nanomedicine.

The present disclosure also relates to a method of preparing the noble metal nanomedicine, the method comprising reducing a noble metal salt with the mixture to form the noble metal nanomedicine and isolating the noble metal nanomedicine.

The present disclosure also relates to a carbon nanomedicine, comprising a carbon nanomaterial having a mean size of 5 to 500 nm, and a mixture of (+)-catechin (2R,3S) and gingerol bound to a surface of the noble metal nanoparticles, the binding occurring non-oxidatively through non-deprotonated alcohol and ether functional groups, π-π interaction, and/or physisorption, wherein the mixture has a catechin to gingerol molar ratio of 5:1 to 1:5, and the mixture makes up at least 50 wt % of all ligands bound to the surface of the carbon nanomaterial, based on a total weight of ligands bound to the surface of the carbon nanomaterial.

In some embodiments, the carbon nanomaterial is at least one selected from the group consisting of fullerenes, graphene particles, graphene oxide particles, reduced graphene oxide particles, carbon nanotubes, carbon dots, and nanodiamonds.

In some embodiments, the carbon nanomaterial is reduced graphene oxide particles.

In some embodiments, the mixture is substantially free of proteins.

In some embodiments, the mixture is substantially free of non-catechin flavonoids.

In some embodiments, the mixture is substantially free of non-(+)-catechin (2R,3S) catechins.

In some embodiments, the mixture is present in an amount of 1 to 50 wt %, based on a total weight of carbon nanomedicine.

The present disclosure also relates to a method of preparing the carbon nanomedicine, the method comprising mixing the carbon nanomaterial with the mixture in a solvent to form the carbon nanomedicine, and isolating the carbon nanomedicine.

In some embodiments, the carbon nanomaterial is reduced graphene oxide and is prepared by a method comprising mixing a carbon source in an acid to form a solution, mixing an oxidant with the solution to form a first suspension, mixing Nigella sativa seed extract with the first suspension to form a second suspension, heating the second suspension at a temperature of 50 to 70° C. to form a third suspension, and adding hydrogen peroxide to the third suspension to form particles of the reduced graphene oxide.

The present disclosure also relates to method of treating obesity, the method comprising administering the noble metal nanomedicine to a subject in need of therapy.

In some embodiments, the noble metal nanomedicine is administered in an amount sufficient to provide 25 to 75 mg of the mixture per kg of subject bodyweight.

The present disclosure also relates to a method of treating obesity, the method comprising administering the carbon nanomedicine to a subject in need of therapy. In some embodiments, the carbon nanomedicine is administered in an amount sufficient to provide 25 to 75 mg of the mixture per kg of subject bodyweight.

DETAILED DESCRIPTION OF THE INVENTION

In the following description, it is understood that other embodiments may be utilized and structural and operational changes may be made without departure from the scope of the present embodiments disclosed herein.

Definitions

As used herein the words "a" and "an" and the like carry the meaning of "one or more."

As used herein, the terms "optional" or "optionally" means that the subsequently described event(s) can or cannot occur or the subsequently described component(s) may or may not be present (e.g., 0 wt. %).

The phrase "substantially free", unless otherwise specified, describes a particular component being present in an amount of less than about 1 wt. %, preferably less than about 0.5 wt. %, more preferably less than about 0.1 wt. %, even more preferably less than about 0.05 wt. %, yet even more preferably 0 wt. %, relative to a total weight of the composition being discussed.

The terms "treating" and "treatment" as used herein refer to reduction in severity and/or frequency of symptoms, elimination of symptoms and/or underlying cause, and improvement or remediation of damage. In certain aspects, the term "treating" and "treatment" as used herein refer to the prevention of the occurrence of symptoms. In other aspects, the term "treating" and "treatment" as used herein refer to the prevention of the underlying cause of symptoms associated with obesity, excess weight, and/or a related condition. Treatment of obesity may involve weight loss or a halt or slowing of weight gain. Such loss or halt or slowing of gain may persist over a treatment duration and/or a post-treatment period.

The phrase "administering to a subject" refers to the process of introducing a composition or dosage form of the invention into the subject (e.g., a human or other mammalian subject) via an art-recognized means of introduction.

According to a first aspect, the present disclosure relates to a nanomedicine comprising a mixture of (+)-catechin (2R,3S) and gingerol.

Mixture of (+)-Catechin (2R,3S) and Gingerol

The term "catechin" is frequently used to described a family of related chemical compounds which are derivatives of flavans that possess a 2-phenyl-3,4-dihydro-2H-chromen-3-ol skeleton (also known as flavan-3-ols). These compounds include catechin, epicatechin, epicatechin gallate, epigallocatechin, epigallocatechin gallate, epiafzelechin, fisetinidol, guibourtinidol, mesquitol, and robinetinidol. The term "catechin" or "catechins" may also refer specifically to the family of flavan-3-ols which consists of catechin (both (+)-catechin (2R,3S) and (−)-catechin (2S3R)), epicatechin (both (+)-epicatechin (2S3S) and (−)-epicatechin (2R,3R)), and the gallate-containing derivatives of catechin including catechin gallate, gallocatechin, epigallocatechin, epicatechin gallate, and epigallocatechin gallate. In some embodiments, the mixture is substantially free of gallate-containing derivatives of catechin such as catechin gallate, gallocatechin, epigallocatechin, epicatechin gallate, and epigallocatechin gallate. In some embodiments, the mixture is substantially free of epicatechin. In preferred embodiments, the mixture is substantially free of (−)-catechin (2S,3R). In some embodiments, the mixture is devoid of epicatechin, and gallate-containing derivatives of catechin such as catechin gallate, gallocatechin, epigallocatechin, epicatechin gallate, and epigallocatechin gallate.

The (+)-catechin (2R,3S) and gingerol should be bound to the surface of the noble metal nanoparticle, the binding occurring non-oxidatively through non-deprotonated alcohol and ether functional groups and/or physisorption, This binding is distinct from oxidative binding seen in, for example, thiol-containing ligands and halides, which produce surface gold atoms which have properties indicative of the gold being in the +1 oxidation state. The non-oxidative binding may occur through metal-ligand coordination type interactions between appropriate functional groups on the (+)-catechin (2R, 3S) and gingerol molecules, particularly alcohol and ether functional groups. The alcohol groups should exist in alcohol form, that is, bearing the hydroxyl proton. Such a form is distinct from the deprotonated alkoxide form. Additionally, there may be non-chemical interactions which cause physisorption of the (+)-catechin (2R, 3S) and gingerol to the surface of the noble metal nanoparticle. Examples of such non-chemical interactions include electrostatic interactions such as ion (or charged species in general)-ion interactions, ion-dipole interactions, or dipole-dipole interactions; and Van der Waals interactions. While the surface of the noble metal nanoparticle may have a charge, preferably the (+)-catechin (2R, 3S), gingerol, or both are present in an uncharged form. Thus, preferably, the interaction between the surface of the noble metal nanoparticle and the (+)-catechin (2R, 3S), gingerol, or both is not of a charged species-charged species electrostatic nature. However, when the surface of the noble metal nanoparticle is charged, there may be electrostatic interaction of a charged species-dipole or dipole-dipole nature.

In some embodiments, the mixture is a phytochemical extract. In this context, "phytochemical extract" may refer to a substance or mixture of substances removed from, collected from, derived from or otherwise obtained from the tissues of a plant by chemical treatment, typically involving treatment with a solvent. In general, a phytochemical extract may be purified with purification treatments which remove components present in an untreated extract which may be considered undesirable for a particular application. These purification treatments, however, do not continue as far as producing a substance which comprises a single phytochemical or multiple members of a related family of phytochemicals in high concentration (e.g. greater than approximately 50 wt %). An extraction and purification treatment protocol which does produce such a substance is typically referred to as "isolation" and the substance itself referred to as an "isolate". In some embodiments, the mixture is a (+)-catechin (2R,3S) and gingerol isolate. In this context, a "(+)-catechin (2R,3S) and gingerol isolate" refers to an isolate comprising (+)-catechin (2R,3S) and gingerol in which the (+)-catechin (2R,3S) and gingerol together comprise at least 50 wt %, preferably at least 55 wt %, preferably at least 60 wt %, preferably at least 65 wt %, preferably at least 70 wt %, preferably at least 75 wt %, preferably at least 80 wt %, preferably at least 85 wt %, preferably at least 90 wt %, preferably at least 95 wt %, preferably at least 97.5 wt %, preferably at least 99 wt % of a total weight of the isolate. The isolate may comprise other phytochemicals or plant components which may be present in a plant extract.

Examples of such other phytochemicals or plant components which may be present in a plant extract/isolate include but are not limited to non-catechin flavonoids, phenolic acids, hydroxycinnamic acids, phenylethanoids, stillbenoids, carotenoids, xanthophylls, betalains, chlrorophylls, tannins, lipids, and proteins.

Examples of non-catechin flavonoids include, but are not limited to anthoxanthins, non-catechin flavans, anthocyanidins, aurones, and chalcones. Examples of anthoxanthins include flavones such as primuletin, chrysin, tectochrysin, primentin, apigenin, acacetin, genkwanin, echioidinin, baicalein, oroxylon, negletein, norwogonin, wogonin, geraldone, tithonine, luteolin, chrysoeriol, diosmetin, pillion, velutin, norartocarpetin, artocarpetin, scutellarein, hispidulin, sorbifolin, pectolinarigenin, cirsimaritin, mikanin, isocutellarein, zapotinin, zapotin, cerrosillin, alnetin, tricin, corymbosin, nepetin, pedalitin, nordifloretin, j aceosidin, cirsiliol, eupatilin, cirsilineol, eupatorin, sinensetin, hypolaetin, onopordin, wightin, nevadensin, xanthomicrol, tangeretin, serpyllin, sudachitin, acerosin, hymenoxin, nobiletin, and scaposin; flavonols such as 3-hydroxyflavone, azaleatin, fisetin, galangin, gossypetin, isorhamnetin, kaempferide, kaempferol, morin, myricetin, natsudaidain, pachypodol, quercetin, rhamnazinm, and rhamnetin; isoflavones such as daidzein, genistein, and orobol; and neoflavonoids such as dalbergichromene, calophyllolide, coutareagenin, dalbergin, and nivetin. Examples of non-catechin flavans include, but are not limited to non-catechin flavanols such as epiafzelechin, fisetinidol, guibourtinidol, mesquitol, robinetinidol, apiforol, and luteoforol; flavan-3, 4-diols such as leucocyanidin, leucodelphinidin, leucofisetinidin, leucomalvidin, leucopelargonidin, leucopeonidin, leucorobinetinidin, melacacidin, and teracacidin; flavanones such as blumeatin, butin, eriodictyol, hesperetin, hesperidin, homoeriodictyol, isosakuranetin, naringenin, naringin, pinocembrin, poncirin, sakuranetin, sakuranin, sterubin, and pinostrobin; and flavanonols such as taxifolin, aromadedrin, and engeletin. Examples of an anthocyanidins include, but are not limited to aurantinidin, capensinidin, cyanidin, delphinidin, europinidin, hirsutidin, malvidin, pelargonidin, peonidin, petunidin, pulchellidin, rosinidin, apigeninidin, columnidin, diosmetinidin, luteolinidin, tricetinidin, apigeninidin, and guibourtinidin. Examples of aurones include, but are not limited to aurone, 4'-chloro-2-hydroxyaurone, 4'-chlroaurone, aureusidin, sulfuretin (6,3',4'-trihydroxyaurone), hispidol (6,4'-dihydroxyaurone), and leptosidin. Examples of chalcones include, but are not limited to aurentiacin A, aurentiacin B, 2',6'-dihydroxy-4'-methoxy-3', 5'-dimethyldihydrochalcone, rubone, bakuchalcone, dihydrochalcone, lapathinol, lapathone, brackenin, mixtecacin, 2',6'-dihydroxy-4'-methoxydihydrochalcone, isoliquiritin, licuraside, xanthangelols B through E, ponganone I and II, stipulin, 3,3'-dihydroxychalcone, spinochalcone A, spinochalcone B, flemistrictin A, calythropsin, dihydrocalythropsin, pedicin, fissistin, isofissistin, munchiwarin, prorepensin, lonchocarpin, and cardamonin.

Examples of phenolic acids include, but are not limited to salicylic acid, vanillin and vanillic acid, gallic acid, ellagic acid, tannic acid.

Examples of hydroxycinnamic acids include, but are not limited to α-cyano-4-hydroxycinnamic acid, caffeic acid, cichoric acid, chlorogenic acid, diferulic acids, coumaric acid, ferulic acid (3-methoxy-4-hydroxycinnamic acid), and sinapinic acid.

Examples of phenylethanoids include, but are not limited to tyrosol, hydroxytyrosol, oleocanthal, and oleuropein.

Examples of stilbenoids include, but are not limited to resveratrol, pterostilbene, piceatannol, and pinosylvin.

Examples of carotenoids include, but are not limited to α-carotene, β-carotene, γ-carotene, δ-carotene, ε-carotene, lycopene, neurosporene, phytofluene, and phytoene.

Examples of xanthophylls include, but are not limited to canthaxanthin, cryptoxanthin, zeaxanthin, astaxanthin, lutein, and rubixanthin.

Examples of betalains include, but are not limited to betanin, isobetanin, probetanin, neobetanin, indicaxanthin, and vulgaxanthin.

Examples of tannins include, but are not limited to ellagitannins tannins such as punicalagins, castalagins, vescalagins, castalins, casuarictins, grandinins, punicalins, roburin As, tellimagrandin IIs, and terflavin Bs; and gallotannins such as digalloyl glucose and 1,3,6-trigalloyl glucose.

In some embodiments, the mixture further comprises one or more other phytochemicals or plant components as described above. In such embodiments, the phytochemicals or plant components also bind to the surface of the noble metal nanoparticles. This binding may be substantially the same as the binding of the (+)-catechin (2R,3S) and gingerol. Alternatively, the binding may be substantially different from the binding of the (+)-catechin (2R,3S) and gingerol. For example, the binding of the other phytochemicals or plant components may occur ionically or oxidatively. Such oxidative binding may occur, for example, through or involving the formation of gold atoms formally in the +1 oxidation state. An example of such oxidative binding is through a thiolate, alkoxide, or amide ion (a deprotonated amine derivative not to be confused with the organic functional group commonly depicted as —C(O)NR$_2$).

As stated above, proteins may be present in a whole plant preparation, a plant extract, or other phytochemical source. Preferably, such proteins are removed from the phytochemical source before such a source is used as the mixture. In some embodiments, the mixture is substantially free of proteins. In some embodiments, the mixture is substantially free of non-flavinoid phytochemicals. In some embodiments, the mixture is substantially free of non-catechin flavonoids. In some embodiments, the mixture is substantially free of non-(+)-catechin (2R,3S) catechins.

In some embodiments, the mixture comprises (+)-catechin (2R,3S) and gingerol in an amount such that the sum of a (+)-catechin (2R,3S) wt % and a gingerol wt % is greater than 90 wt %, preferably greater than 91 wt %, preferably greater than 92%, preferably greater than 93 wt %, preferably greater than 94 wt %, preferably greater than 95 wt %, preferably greater than 96 wt %, preferably greater than 97 wt %, preferably greater than 97.5 wt %, preferably greater than 98 wt %, preferably greater than 98.5 wt %, preferably greater than 99 wt %, preferably greater than 99.25 wt %, preferably greater than 99.5 wt %, preferably greater than 99.75 wt %, preferably greater than 99.9 wt %, based on a total weight of mixture. In some embodiments, the bioactive phytochemical mixture consists of (+)-catechin (2R,3S) and gingerol. In such embodiments, purified (+)-catechin (2R,3S) and purified gingerol may be mixed together to form the mixture. The (+)-catechin (2R,3S) and/or gingerol may be synthesized using chemical synthesis techniques known to one of ordinary skill in the art. Alternatively, the (+)-catechin (2R,3S) and/or gingerol may be isolated and further purified from a plant or plants.

In some embodiments, the mixture has a (+)-catechin (2R,3S) to gingerol molar ratio of 5:1 to 1:5, preferably 4.5:1 to 1:4.5, preferably 4:1 to 1:4, preferably 3.5:1 to 1:3.5, preferably 2:1 to 1:2, preferably 1.75:1 to 1:1.75, preferably 1.5:1 to 1:1.5, preferably 1.25:1 to 1:1.25, preferably 1.1:1 to 1:1.1, preferably 1:1.

Noble Metal Nanomedicine

In some embodiments the nanomedicine is a noble metal nanomedicine, comprising noble metal nanoparticles comprising a noble metal and having surface ligands comprising the mixture comprising (+)-catechin (2R,3S) and gingerol. The noble metal may be at least one selected from the group consisting of ruthenium, rhodium, palladium, osmium, iridium, platinum, gold, and silver. In preferred embodiments, the noble metal is at least one selected from the group consisting of gold, silver, and platinum. The term "noble metal nanoparticle" as used herein refers to an noble metal rich material (i.e. greater than 50%, more preferably greater than 60%, more preferably greater than 70%, more preferably greater than 75%, more preferably greater than 80%, more preferably greater than 85%, more preferably greater than 90%, more preferably greater than 95%, most preferably greater than 99% noble metal by weight, the noble metal being at least one selected from the list above).

In addition to the noble metal, various non-noble metal materials including, but not limited to, alloys, non-noble metals, metalloids, and non-metals may be present in the noble metal nanoparticles. The total weight of these non-noble metal materials relative to the total weight percentage of the noble metal in the nanoparticles is typically less than 30%, preferably less than 20%, preferably less than 15%, preferably less than 10%, more preferably less than 5%, more preferably less than 4%, more preferably less than 3%, more preferably less than 2%, more preferably less than 1%.

In addition to the noble metal(s), it is envisaged that the present disclosure may be adapted to incorporate noble metal alloys as the noble metal nanoparticles. Exemplary alloys include, but are not limited to: gold alloys with copper and silver (colored gold, crown gold, electrum), gold alloys with rhodium (rhodite), gold alloys with copper (rose gold, tumbaga), gold alloys with nickel and palladium (white gold), gold alloys including the addition of platinum, manganese, aluminum, iron, indium and other appropriate elements or mixtures thereof, silver alloys with copper (shibuichi, sterling silver, Tibetan silver, Britannia silver), silver alloys with copper and gold (goloid), silver alloys with copper and germanium (argentium sterling silver), silver alloys with platinum (platinum sterling), silver alloys with copper (silver graphite), silver alloys including the addition of palladium, zinc, iridium, and tin and other appropriate elements or mixtures thereof, platinum alloys with gold, platinum alloys with cobalt, platinum alloys with rare earth elements, and platinum alloys with nickel. In one embodiment, it is envisaged that the present disclosure may be adapted in such a manner that the noble metal nanoparticles substantially comprise a noble metal alloy.

In general, the noble metal nanoparticles can be any shape known to one of ordinary skill in the art. Examples of suitable shapes the noble metal nanoparticles may take include spheres, spheroids, lentoids, ovoids, solid polyhedra such as tetrahedra, cubes, octahedra, icosahedra, dodecahedra, hollow polyhedral (also known as nanocages), stellated polyhedral (both regular and irregular, also known as nanostars), triangular prisms (also known as nanotriangles), hollow spherical shells (also known as nanoshells), tubes (also known as nanotubes), nanosheets, nanoplatelets, nanodisks, rods (also known as nanorods), and mixtures thereof. In the case of nanorods, the rod shape may be defined by a ratio of a rod length to a rod width, the ratio being known as the aspect ratio. For noble metal nanoparticles of the current invention, nanorods should have an aspect ratio less than 1000, preferably less than 750, preferably less than 500, preferably less than 250, preferably less than 100, preferably less than 75, preferably less than 50, preferably less than 25. Nanorods having an aspect ratio greater than 1000 are typically referred to as nanowires and are not a shape that the noble metal nanoparticles are envisioned as having in any embodiments.

In some embodiments, the noble nanoparticles have uniform shape. Alternatively, the shape may be non-uniform. As used herein, the term "uniform shape" refers to an average consistent shape that differs by no more than 10%, by no more than 5%, by no more than 4%, by no more than 3%, by no more than 2%, by no more than 1% of the distribution of noble metal nanoparticles having a different shape. As used herein, the term "non-uniform shape" refers to an average consistent shape that differs by more than 10% of the distribution of gold nanoparticles having a different shape. In one embodiment, the shape is uniform and at least 90% of the noble nanoparticles are spherical or substantially circular, and less than 10% are polygonal. In another embodiment, the shape is non-uniform and less than 90% of the noble metal nanoparticles are spherical or substantially circular, and greater than 10% are polygonal.

In some embodiments, the noble metal nanoparticles have a mean particle size of 5 to 500 nm, preferably 7.5 to 475 nm, preferably 10 to 450 nm, preferably 12.5 to 425 nm, preferably 15 to 400 nm, preferably 17.5 to 375 nm, preferably 20 to 350 nm, preferably 25 to 325 nm, preferably 30 to 300 nm, preferably 40 to 275 nm, preferably 50 to 250 nm. In embodiments where the noble metal nanoparticles are spherical, the particle size may refer to a particle diameter. In embodiments where the noble metal nanoparticles are polyhedral, the particle size may refer to the diameter of a circumsphere. In some embodiments, the particle size refers to a mean distance from a particle surface to particle centroid or center of mass. In alternative embodiments, the particle size refers to a maximum distance from a particle surface to a particle centroid or center of mass. In some embodiments where the noble metal nanoparticles have an anisotropic shape such as nanorods, the particle size may refer to a length of the nanorod, a width of the nanorod, or an average of the length and width of the nanorod. In some embodiments, the particle size refers to the diameter of a sphere having an equivalent volume as the particle.

In some embodiments, the noble metal nanoparticles of the present disclosure are monodisperse, having a coefficient of variation or relative standard deviation, expressed as a percentage and defined as the ratio of the particle size standard deviation ($\sigma$) to the particle size mean ($\mu$) multiplied by 100 of less than 25%, preferably less than 10%, preferably less than 8%, preferably less than 6%, preferably less than 5%, preferably less than 4%, preferably less than 3%, preferably less than 2%. In some embodiments, the noble metal nanoparticles of the present disclosure are monodisperse having a particle size distribution ranging from 80% of the average particle size to 120% of the average particle size, preferably 90-110%, preferably 95-105% of the average particle size. In some embodiments, the noble metal nanoparticles are not monodisperse.

In general, the particle size may be determined by any suitable method known to one of ordinary skill in the art. In some embodiments, the particle size is determined by powder X-ray diffraction (PXRD). Using PXRD, the particle size may be determined using the Scherrer equation, which relates the full-width at half-maximum (FWHM) of diffraction peaks to the size of regions comprised of a single crystalline domain (known as crystallites) in the sample. In some embodiments, the crystallite size is the same as the particle size. For accurate particle size measurement by PXRD, the particles should be crystalline, comprise only a single crystal, and lack non-crystalline portions. Typically, the crystallite size underestimates particle size compared to other measures due to factors such as amorphous regions of particles, the inclusion of non-crystalline material on the surface of particles such as bulky surface ligands, and particles which may be composed of multiple crystalline domains. In some embodiments, the particle size is determined by dynamic light scattering (DLS). DLS is a technique which uses the time-dependent fluctuations in light scattered by particles in suspension or solution in a solvent, typically water to measure a size distribution of the particles. Due to the details of the DLS setup, the technique measures a hydrodynamic diameter of the particles, which is the diameter of a sphere with an equivalent diffusion coefficient as the particles. The hydrodynamic diameter may include factors not accounted for by other methods such as non-crystalline material on the surface of particles such as bulky surface ligands, amorphous regions of particles, and surface ligand-solvent interactions. Further, the hydrodynamic diameter may not accurately account for non-spherical particle shapes. DLS does have an advantage of being able to account for or more accurately model solution or suspension behavior of the particles compared to other techniques. In some embodiments, the particle size is determined by electron microscopy techniques such as scanning electron microscopy (SEM) or transmission electron microscopy (TEM).

In some embodiments, the noble metal nanoparticles further comprise surface ligands which are not present in the mixture. In general, the surface ligands may be any suitable surface ligands known to one of ordinary skill in the art. Examples of such surface ligands include, but are not limited to carboxylates (often referred to by their acid forms) such as citrate (citric acid), oleate (oleic acid), amines such as oleylamine, hexadecylamine, octadecylamine, and 1,6-diaminohexane; thiols such as decanethiol, dodecanethiol, and thiol-terminated polyethylene glycol (PEG-SH); lipids, proteins such as albumin, ovalbumin, thrombin, and lactoglobulin, polysaccharides such as chitosan and dextran; phosphines such as trioctylphosphine, trioctylphosphine oxide, and triphenylphosphine; and surfactants such as cetyltrimethylammonium bromide (CTAB). For examples of surface ligands (also called capping ligands or capping agents), see Javed, et. al., Kobayashi, et. al., and Guerrini, et. al. [Javed, R., et. al., Journal of Nanobiotechnology, 2020, 18, article number 172; Kobayashi, K., et. al., Polymer Journal, 2014, 46, 460-468; and Guerrini, L., et. al., Materials, 2018, 11, 1154].

In some embodiments, the noble metal nanoparticles have a coating. In such embodiments, the noble metal nanoparticle should be understood to comprise a noble metal portion and a coating portion. That is, the coating forms an integral part of the noble metal nanoparticle. In embodiments where the noble metal nanoparticles have a coating, the "surface of the noble metal nanoparticle" should be understood to mean a surface of the coating portion, a surface of the noble metal portion, or both. In some embodiments, the mixture is attached to, disposed upon, acting as a surface ligand for, or otherwise interacting with the coating portion of the noble metal nanoparticle. In some embodiments, the mixture is attached to, disposed upon, acting as a surface ligand for, or otherwise interacting with the noble metal portion of the noble metal nanoparticle. In such embodiments, the coating should not prevent the mixture from direct interaction with the noble metal portion of the noble metal nanoparticle. In some embodiments, the coating is porous, the pores allowing for direct interaction of the mixture and the noble metal portion. Alternatively, the coating may be attached to, disposed upon, encapsulating, or otherwise interacting with the mixture, which is itself in direct contact with the noble metal portion. Such embodiments may be thought of as sandwiching the mixture between the noble metal portion and the coating portion. Examples of materials which may comprise the coating include, but are not limited to silica, lipids, polymers, and carbon nanomaterials. In general, the polymer may be any suitable polymer known to one or ordinary skill in the art. Examples of such suitable polymer include, but are not limited to polycarboxylic acid polymers and copolymers including polyacrylic acids; acetal polymers and copolymers; acrylate and methacrylate polymers and copolymers (e.g., n-butyl methacrylate); cellulosic polymers and copolymers, including cellulose acetates, cellulose nitrates, cellulose propionates, cellulose acetate butyrates, cellophanes, rayons, rayon triacetates, and cellulose ethers such as carboxymethyl celluloses and hydoxyalkyl celluloses; polyoxymethylene polymers and copolymers; polyimide polymers and copolymers such as polyether block imides, polyamidimides, polyesterimides, and polyetherimides; polysulfone polymers and copolymers including polyarylsulfones and polyethersulfones; polyamide polymers and copolymers including nylon 6,6, nylon 12, polycaprolactams and polyacrylamides; resins including alkyd resins, phenolic resins, urea resins, melamine resins, epoxy resins, allyl resins and epoxide resins; polycarbonates; polyacrylonitriles; polyvinylpyrrolidones (crosslinked and otherwise); polymers and copolymers of vinyl monomers including polyvinyl alcohols, polyvinyl halides such as polyvinyl chlorides, ethylene-vinylacetate copolymers (EVA), polyvinylidene chlorides, polyvinyl ethers such as polyvinyl methyl ethers, polystyrenes, styrene-maleic anhydride copolymers, styrene-butadiene copolymers, styrene-ethylene-butylene copolymers (e.g., a polystyrenepolyethylene/butylene-polystyrene (SEBS) copolymer, available as Kraton® G series polymers), styrene-isoprene copolymers (e.g., polystyrene-polyisoprene-polystyrene), acrylonitrile-styrene copolymers, acrylonitrile-butadiene-styrene copolymers, styrene-butadiene copolymers and styrene-isobutylene copolymers (e.g., polyisobutylene-polystyrene block copolymers such as SIBS), polyvinyl ketones, polyvinylcarbazoles, and polyvinyl esters such as polyvinyl acetates; polybenzimidazoles; ionomers; polyalkyl oxide polymers and copolymers including polyethylene oxides (PEO); glycosaminoglycans; polyesters including polyethylene terephthalates and aliphatic polyesters such as polymers and copolymers olfactive (which includes lactic acid as well as d-, l- and mesa lactide), epsilon-caprolactone, glycolide (including glycolic acid), hydroxybutyrate, hydroxyvalerate, para-dioxanone, trimethylene carbonate (and its alkyl derivatives), 1,4-dioxepan-2-one, 1,5-dioxepan-2-one, and 6,6-dimethyl-1,4-dioxan-2-one (a copolymer of polylactic acid and polycaprolactone is one specific example); polyether polymers and copolymers including polyarylethers such as polyphenylene ethers, polyether ketones, polyether ether ketones; polyphenylene sulfides; polyisocyanates; polyolefin polymers and copolymers, including polyalkylenes such as polypropylenes, polyethylenes (low and high density, low and high molecular weight), polybutylenes (such as polybut-1-ene and polyisobutylene), poly-4-methyl-pen-1-enes, ethylene-alpha-olefin copolymers, ethylene-methyl methacrylate copolymers and ethylene-vinyl acetate copolymers; polyolefin elastomers (e.g., santoprene), ethylene propylene diene monomer (EPDM) rubbers, fluorinated polymers and copolymers, including polytetrafluoroethylenes (PTFE), poly(tetrafluoroethylene-co-hexafluoropropene) (FEP), modified ethylene-tetrafluoroethylene copolymers (ETFE), and polyvinylidene fluorides (PVDF); silicone polymers and copolymers; polyurethanes; p-xylylene polymers; polyiminocarbonates; copoly(ether-esters) such as polyethylene oxide-polylactic acid copolymers; polyphosphazines; polyalkylene oxalates; polyoxaamides and polyoxaesters (including those containing amines and/or amido groups); polyorthoesters; biopolymers, such as polypeptides, proteins, polysaccharides and fatty acids (and esters thereof), including fibrin, fibrinogen, collagen, elastin, chitosan, gelatin, starch, glycosaminoglycans such as hyaluronic acid; as well as blends and further copolymers of the above. The coating may be intended to be broken down, degraded, disintegrated, or otherwise removed from the noble metal nanoparticle in whole or in part. Such removal may cause or coincide with release of the bioactive phytochemical mixture from the noble metal nanoparticle. In preferred embodiments, the noble metal nanomedicine is substantially free of a coating.

In some embodiments, the mixture is present in an amount of 1 to 50 wt %, preferably 2.5 to 47.5 wt %, preferably 5 to 45 wt %, preferably 7.5 to 42.5 wt %, preferably 10 to 40 wt %, preferably 12.5 to 38.5 wt %, preferably 15 to 35 wt %, based on a total weight of noble metal nanomedicine.

The present disclosure also relates to a method of preparing the noble metal nanomedicine, the method comprising reducing a noble metal salt with the mixture to form the noble metal nanomedicine and isolating the noble metal nanomedicine. In some embodiments, the reducing takes place in a solvent. In general, the solvent may be any suitable solvent known to one of ordinary skill in the art. Examples of suitable solvents include, but are not limited to water; alcohols such as methanol, ethanol, and isopropanol; ethers such as diethyl ether, tetrahydrofuran, and dioxane; dimethylsulfoxide; acetone; ethyl acetate; dimethylformamide; acetonitrile; and mixtures thereof. In preferred embodiments, the solvent is water. In general, the noble metal salt may be any suitable noble metal salt known to one of ordinary skill in the art. Examples of suitable noble metal salts include halide salts such as iodides, chlorides, and bromides; nitrate salts; acetate salts; trifluoroacetate salts; oxalate salts; and mixtures thereof. In some preferred embodiments where the noble metal is gold, the gold salt is gold (III) chloride or a hydrate thereof. In some preferred embodiments where the noble metal is silver, the silver salt is silver nitrate or a hydrate thereof. In some embodiments, the method further comprises use of a supplementary reducing agent used with the mixture. In general, the supplementary reducing agent may be any suitable reducing agent known to one of ordinary skill in the art. Examples of such reducing agents include, but are not limited to, borohydrides; citrates; ascorbates; amines such as 4-aminophenol, oleylamine, trimethylamine, and indole; amino acids such as glycine, tryptophan, and proline; and hydrogen. In preferred embodiments, the method is devoid of supplementary reducing agents. In some embodiments, the reducing is performed at 20 to 100° C., preferably 21 to 90° C., preferably 23 to 80° C., preferably 25 to 75° C. In general, the isolating may be performed by suitable technique or combination of techniques known to one of ordinary skill in the art. Examples of such techniques include, but are not limited to, liquid-liquid extraction, dialysis, centrifugation, chromatography, precipitation, filtration, and decantation. In some embodiments, the isolating comprises washing. In general, the washing may be performed using any suitable technique known to one of ordinary skill in the art. In some embodiments, the washing is performed with a wash solvent which may be any suitable solvent as described above. In some embodiments, multiple rounds of washing are performed. These multiple rounds may be performed with the same wash solvent or with different wash solvents.

Carbon Nanomedicine

In some embodiments, the nanomedicine is a carbon nanomedicine, comprising a carbon nanomaterial and an adsorbed mixture comprising (+)-catechin (2R,3S) and gingerol. In general, the mixture is the same as the mixture as described above. In general, the carbon nanomaterial may be any suitable carbon nanomaterial known to one of ordinary skill in the art. Examples of carbon nanomaterials include carbon nanotubes, fullerenes, fullerene whiskers, carbon nanobuds, carbon nanoscrolls, carbon dots, activated carbon, carbon black, graphene, graphene oxide, reduced graphene oxide, and nanodiamonds. In some embodiments, the carbon nanomaterial is at least one selected from the group consisting of fullerenes, graphene, graphene oxide, reduced graphene oxide, carbon nanotubes, carbon dots, and nanodiamonds.

In some embodiments, the carbon nanomaterial is carbon nanotubes. The carbon nanotubes may, in general, be any suitable carbon nanotubes known to one of ordinary skill in the art. Carbon nanotubes may be classified by structural properties such as the number of walls or the geometric configuration of the atoms that make up the nanotube. Classified by their number of walls, the carbon nanotubes can be single-walled carbon nanotubes (SWCNT) which have only one layer of carbon atoms arranged into a tube, or multi-walled carbon nanotubes (MWCNT), which have more than one single-layer tube of carbon atoms arranged so as to be nested, one tube inside another, each tube sharing a common orientation. Closely related to MWNTs are carbon nanoscrolls. Carbon nanoscrolls are structures similar in shape to a MWCNT, but made of a single layer of carbon atoms that has been rolled onto itself to form a multi-layered tube with a free outer edge on the exterior of the nanoscroll and a free inner edge on the interior of the scroll and open ends. The end-on view of a carbon nanoscroll has a spiral-like shape. For the purposes of this disclosure, carbon nanoscrolls are considered a type of MWCNT. Classified by the geometric configuration of the atoms that make up the nanotube, carbon nanotubes can be described by a pair of integer indices n and m. The indices n and m denote the number of unit vectors along two directions in the honeycomb crystal lattice of a single layer of carbon atoms. If m=0, the nanotubes are called zigzag type nanotubes. If n=m, the nanotubes are called armchair type nanotubes. Otherwise they are called chiral type nanotubes. In some embodiments, the carbon nanotubes are metallic. In other embodiments, the carbon nanotubes are semiconducting. In some embodiments, the carbon nanotubes are SWCNTs. In other embodiments, the carbon nanotubes are MWCNTs. In some embodiments, the carbon nanotubes are carbon nanoscrolls. In some embodiments, the carbon nanotubes are zigzag type nanotubes. In alternative embodiments, the carbon nanotubes are armchair type nanotubes. In other embodiments, the carbon nanotubes are chiral type nanotubes.

In some embodiments, the carbon nanomaterial is a fullerene. Fullerenes are molecules which consist of carbon atoms connected by single and double bonds so as to form a closed or partially closed mesh, with fused rings of five to seven atoms. Fullerenes may be hollow spheres like $C_{60}$, ellipsoids like $C_{70}$, or other shapes. Fullerenes typically have diameters of 0.3 nm to 2.4 nm. Examples of fullerenes include $C_{20}$, $C_{30}$, $C_{70}$, $C_{80}$, $C_{90}$, $C_{100}$, $C_{180}$, $C_{240}$, $C_{260}$, $C_{320}$, $C_{500}$, $C_{540}$, and $C_{720}$. Fullerenes frequently exist as agglomerates of individual fullerene molecules. Such agglomerates may be formed from a single type of fullerene or from multiple types of fullerenes. Such agglomerates may have sizes of 5 to 500 nm, preferably 7.5 to 475 nm, preferably 10 to 450 nm, preferably 12.5 to 425 nm, preferably 15 to 400 nm, preferably 17.5 to 375 nm, preferably 20 to 350 nm, preferably 25 to 325 nm, preferably 30 to 300 nm, preferably 40 to 275 nm, preferably 50 to 250 nm.

In some embodiments, the carbon nanomaterial is graphene. In some embodiments, the carbon nanomaterial is graphene nanosheets. Graphene nanosheets may consist of stacks of graphene sheets, the stacks having an average thickness and a diameter. In some embodiments, the stacks comprise 1 to 60 sheets of graphene, preferably 2 to 55 sheets of graphene, preferably 3 to 50 sheets of graphene. In some embodiments, the graphene nanosheets have a thickness of 0.33 to 25 nm, preferably 0.66 to 22.5 nm, preferably 1 to 20 nm, preferably 1.33 to 17.5 nm. In some embodiments, the graphene nanosheets have a diameter of 5 to 500 nm, preferably 7.5 to 475 nm, preferably 10 to 450 nm, preferably 12.5 to 425 nm, preferably 15 to 400 nm, preferably 17.5 to 375 nm, preferably 20 to 350 nm, preferably 25 to 325 nm, preferably 30 to 300 nm, preferably 40 to 275 nm, preferably 50 to 250 nm. In some embodiments, the graphene nanosheets have a monodisperse thickness, having a coefficient of variation or relative standard deviation, expressed as a percentage and defined as the ratio of the graphene nanosheet thickness standard deviation ($\sigma$) to the graphene nanosheet thickness mean ($\mu$), multiplied by 100%, of less than 25%, preferably less than 10%, preferably less than 8%, preferably less than 6%, preferably less than 5%. In a preferred embodiment, the graphene nanosheets have a monodisperse thickness, having a size distribution ranging from 80% of the average thickness to 120% of the average thickness, preferably 85 to 115%, preferably 90 to 110% of the average thickness. In another embodiment, the graphene nanosheets do not have a monodisperse thickness. In some embodiments, the graphene nanosheets have a monodisperse diameter, having a coefficient of variation or relative standard deviation, expressed as a percentage and defined as the ratio of the graphene nanosheet diameter standard deviation ($\sigma$) to the graphene nanosheet diameter mean ($\mu$), multiplied by 100%, of less than 25%, preferably less than 10%, preferably less than 8%, preferably less than 6%, preferably less than 5%. In a preferred embodiment, the graphene nanosheets have a monodisperse diameter, having a size distribution ranging from 80% of the average diameter to 120% of the average diameter, preferably 85 to 115%, preferably 90 to 110% of the average diameter. In another embodiment, the graphene nanosheets do not have a monodisperse diameter.

In alternative embodiments, the graphene is in the form of graphene particles. In some embodiments, the graphene particles have an average particle size of 5 to 500 nm, preferably 7.5 to 475 nm, preferably 10 to 450 nm, preferably 12.5 to 425 nm, preferably 15 to 400 nm, preferably 17.5 to 375 nm, preferably 20 to 350 nm, preferably 25 to 325 nm, preferably 30 to 300 nm, preferably 40 to 275 nm, preferably 50 to 250 nm. The graphene particles may have a spherical shape, or may be shaped like blocks, flakes, ribbons, discs, granules, platelets, angular chunks, rectangular prisms, or some other shape. In some embodiments, the graphene particles may be substantially spherical, meaning that the distance from the graphene particle centroid (center of mass) to anywhere on the graphene outer surface varies by less than 30%, preferably by less than 20%, more preferably by less than 10% of the average distance. In some embodiments, the graphene particles are in the form of flakes, ribbons, discs, or platelets having a mean size in a range as previously described and having a largest dimension that is 50 to 500%, preferably 75 to 400, preferably 100 to 350%, preferably 150 to 250% of the range previously described and a smallest dimension that is 0.01 to 100%, preferably 0.1 to 50%, preferably 0.5 to 25%, preferably 1 to 10% of the range previously described. In some embodiments, the graphene particles may be in the form of agglomerates. As used herein, the term "agglomerates" refers to a clustered particulate composition comprising primary particles, the primary particles being aggregated together in such a way so as to form clusters thereof, at least 50 volume percent of the clusters having a mean size that is at least 2 times the mean size of the primary particles, and preferably at least 90 volume percent of the clusters having a mean size that is at least 5 times the mean size of the primary particles. The primary particles may be the graphene particles having a mean size as previously described. In some embodiments, the graphene particles are monodisperse, having a coefficient of variation or relative standard deviation, expressed as a percentage and defined as the ratio of the graphene particle size standard deviation ($\sigma$) to the graphene particle size mean ($\mu$), multiplied by 100%, of less than 25%, preferably less than 10%, preferably less than 8%, preferably less than 6%, preferably less than 5%. In a preferred embodiment, the graphene particles are monodisperse, having a graphene particle size distribution ranging from 80% of the average particle size to 120% of the average particle size, preferably 85 to 115%, preferably 90 to 110% of the average particle size. In another embodiment, the graphene particles are not monodisperse.

In some embodiments, the graphene is pristine graphene. Pristine graphene refers to graphene that has not been oxidized or otherwise functionalized. Pristine graphene may be obtained by methods such as exfoliation, chemical vapor deposition synthesis, opening of carbon nanotubes, unrolling of carbon nanoscrolls, and the like. In alternative embodiments, the graphene is functionalized graphene. Functionalized graphene is distinguished from pristine graphene by the presence of functional groups on the surface or edge of the graphene that contain elements other than carbon and hydrogen. In other alternative embodiments, the graphene is graphene oxide. Graphene oxide refers to graphene that has various oxygen-containing functionalities that are not present in pristine graphene. Examples of such oxygen-containing functionalities include epoxides, carbonyl, carboxyl, and hydroxyl functional groups. Graphene oxide is sometimes considered to be a type of functionalized graphene.

In other alternative embodiments, the graphene is reduced graphene oxide. Reduced graphene oxide (rGO) refers to graphene oxide that has been chemically reduced. It is distinct from graphene oxide in it contains substantially fewer oxygen-containing functionalities compared to graphene oxide, and it is distinct from pristine graphene by the presence of oxygen-containing functionalities and structural defects in the carbon network. Reduced graphene oxide is sometimes considered to be a type of functionalized graphene. In preferred embodiments, the carbon nanomaterial is reduced graphene oxide. The reduced graphene oxide may exist as nanosheets as described above, particles having a spherical shape, or may be shaped like blocks, flakes, ribbons, discs, granules, platelets, angular chunks, rectangular prisms, or some other shape as described above, agglomerates as described above, or any other shape known to one of ordinary skill in the art.

In some embodiments, the particles of a carbon nanomaterial are a single type of particle as described above. In this context, "a single type of particle" may refer to particles of a single carbon nanomaterial, particles which have substantially the same shape, particles which have substantially the same size, or any combination of these. In alternative embodiments, mixtures of types of particles are used.

In some embodiments, the particles of the carbon nanomaterial further comprise surface ligands which are not the mixture as described above. In some embodiments, the particles of the carbon nanomaterial have a coating as described above.

In some embodiments, the mixture is present in an amount of 1 to 50 wt %, preferably 2.5 to 47.5 wt %, preferably 5 to 45 wt %, preferably 7.5 to 42.5 wt %, preferably 10 to 40 wt %, preferably 12.5 to 38.5 wt %, preferably 15 to 35 wt %, based on a total weight of carbon nanomedicine.

The present disclosure also relates to a method of preparing the carbon nanomedicine, the method comprising mixing particles of a carbon nanomaterial with the mixture in a solvent to form the carbon nanomedicine and isolating the carbon nanomedicine. In general, the solvent may be any suitable solvent known to one of ordinary skill in the art as described above. In general, the isolating may be performed by suitable technique or combination of techniques known to one of ordinary skill in the art, as described above.

In some embodiments, the carbon nanomaterial is reduced graphene oxide. In general, the reduced graphene oxide may be prepared by any suitable method known to one of ordinary skill in the art. Examples of such methods include electrochemical reduction of graphene oxide or graphite oxide and treatment of graphene oxide or graphite oxide with a suitable reducing agent, such as hydrazine, ascorbic acid, sodium borohydride, or a phytochemical extract. In some embodiments, the reduced graphene oxide is prepared by a method comprising mixing a carbon source in an acid to form a solution, mixing an oxidant with the solution to form a first suspension, mixing Nigella *sativa* seed extract with the first suspension to form a second suspension, heating the second suspension at a temperature of 50 to 70° C. to form a third suspension, and adding hydrogen peroxide to the third suspension to form particles of the reduced graphene oxide. Further details of this method may be found in U.S. Pat. No. 9,688,539 B1, incorporated herein by reference in its entirety.

In general, the interaction between the (+)-catechin (2R, 3S), gingerol, or both and the carbon nanomaterial may be substantially the same as the interaction with the noble metal nanoparticles as described above. Additionally, there may be chemisorptive interactions between distinct functional groups present on the carbon nanomaterial and functional groups present on the (+)-catechin (2R, 3S), gingerol, or both. Examples of such interactions include oriented dipole-dipole interactions and hydrogen bonding. Additionally, because the carbon nanomaterial may have an region characterized by a π-electron system, there may be 7E-7E interactions between the carbon nanomaterial and the (+)-catechin (2R, 3S), gingerol, or both.

Method of Treating Obesity

The present disclosure also relates to a method of treating obesity, the method comprising administering the noble metal nanomedicine to a subject in need of therapy. In general, the administering may be performed by any route known to one of ordinary skill in the art.

In some embodiments, the noble metal nanomedicine is administered as a pharmaceutical composition comprising the noble metal nanomedicine. In some embodiments, the pharmaceutical composition further comprises a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. The use of such media and agents for pharmaceutically active substances is well known in the art. Except insofar as any conventional media or agent is incompatible with the active compound, use thereof in the compositions is contemplated. Supplementary active compounds can also be incorporated into the compositions. Modifications can be made to the noble metal nanomedicine of the present invention to affect solubility or clearance of the compound, for example additional surface ligands and/or coatings.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, rectal administration, and direct injection into the affected area, such as direct injection into the digestive system. Solutions or suspensions used for parenteral, intradermal, or subcutaneous application can include the following components: a sterile diluent such as water for injection, saline solution, fixed oils, polyethylene glycols, glycerin, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, or phosphate buffered saline (PBS). In all cases, the composition must be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the noble metal nanomedicine in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the noble metal nanomedicine plus any additional desired ingredient from a previously sterile-filtered solution thereof.

Oral compositions generally include an inert diluent or an edible carrier. The oral compositions can be enclosed in gelatin capsules or compressed into tablets. For the purpose of oral therapeutic administration, the noble metal nanomedicine can be incorporated with excipients and used in the form of tablets, troches, or capsules. Oral compositions can also be prepared using a fluid carrier, wherein the noble metal nanomedicine in the fluid carrier is applied orally and swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the noble metal nanomedicine is delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the noble metal nanomedicine is formulated into ointments, salves, gels, or creams as generally known in the art.

The noble metal nanomedicine can also be prepared in the form of suppositories (e.g., with conventional suppository bases such as cocoa butter and other glycerides) or retention enemas for rectal delivery.

In one embodiment, the noble metal nanomedicine is prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved, and the limitations inherent in the art of compounding such an active compound for the treatment of individuals. Dosage unit forms include solid dosage forms, like tablets, powders, capsules, suppositories, sachets, troches and losenges as well as liquid suspensions and elixirs. Capsule dosages, of course, will contain the noble metal nanomedicine within a capsule which may be made of gelatin or other conventional encapsulating material. Tablets and powders may be coated. Tablets and powders may be coated with an enteric coating. The enteric coated powder forms may have coatings comprising phthalic acid cellulose acetate, hydroxypropylmethyl-cellulose phthalate, polyvinyl alcohol phthalate, carboxymethylethylcellulose, a copolymer of styrene and maleic acid, a copolymer of methacrylic acid and methyl methacrylate, and like materials, and if desired, they may be employed with suitable plasticizers and/or extending agents. A coated tablet may have a coating on the surface of the tablet or may be a tablet comprising a powder or granules with an enteric-coating.

The dosage forms include dosage forms suitable for oral, buccal, rectal, parenteral (including subcutaneous, intramuscular, and intravenous), inhalant and ophthalmic administration. Although the most suitable route in any given case will depend on the nature and severity of the condition being treated, the most preferred route of the present invention is oral. The noble metal nanomedicine may be conveniently presented in unit dosage form and prepared by any of the methods well-known in the art of pharmacy.

In some embodiments, the noble metal nanomedicine is administered in an amount sufficient to provide 25 to 75 mg, preferably 30 to 70 mg, preferably 35 to 65 mg, preferably 40 to 60 mg, preferably 45 to 55 mg, preferably 47.5 to 52.5 mg, preferably 49 to 51 mg, preferably 50 mg of the mixture per kg of subject bodyweight.

In some embodiments, the administration is via an oral route. In some embodiments, oral administration occurs once per day. Alternatively, oral administration may occur more than once per day, for example twice, three times, or four times per day. Preferably, such occurrences should be spread out across the day. In some embodiments, the oral administration preferably occurs at a meal time. In such embodiments, the administration may occur before, during, or after a meal. In some embodiments, the administration is repeated on consecutive days for the entirety of a treatment duration. In general, the treatment duration may be any suitable length of time, or example days, weeks, months, or years. Alternatively, the treatment duration may be a suitable duration as determined by a qualified medical professional. In some embodiments, the treatment may persist after weight loss to a target weight has occurred (e.g. when a patient is no longer obese). In alternative embodiments, the treatment may halt after weight loss to a target weight has occurred.

The present disclosure also relates to a method of treating obesity, the method comprising administering the carbon nanomedicine to a subject in need of therapy. The administering may be any suitable administering known to one of ordinary skill in the art as described above.

In some embodiments, the carbon nanomedicine is administered in an amount sufficient to provide 25 to 75 mg, preferably 30 to 70 mg, preferably 35 to 65 mg, preferably 40 to 60 mg, preferably 45 to 55 mg, preferably 47.5 to 52.5 mg, preferably 49 to 51 mg, preferably 50 mg of the mixture per kg of subject bodyweight.

Where a numerical limit or range is stated herein, the endpoints are included. Also, all values and subranges within a numerical limit or range are specifically included as if explicitly written out.

Obviously, numerous modifications and variations of the present invention are possible in light of the above teachings. It is therefore to be understood that, within the scope of the appended claims, the invention may be practiced otherwise than as specifically described herein.

The invention claimed is:

1. A noble metal nanomedicine, comprising:
   nanoparticles of at least one metal selected from the group consisting of gold, silver, and platinum and having a mean particle size of 5 to 500 nm;
   a mixture of (+)-catechin (2R,3S) and gingerol bound to a surface of the noble metal nanoparticles, the binding occurring non-oxidatively through non-deprotonated alcohol and ether functional groups of the (+)-catechin (2R,3S) and gingerol to the noble metal nanoparticles; and
   one or more additional surface ligands selected from the group consisting of a carboxylate, an amine, a polysaccharide and a phosphine,
   wherein:
   the mixture has a catechin to gingerol molar ratio of 5:1 to 1:5 and is substantially free of proteins;
   the mixture makes up at least 50 wt % of all ligands bound to the surface of the noble metal nanoparticles, based on a total weight of ligands bound to the surface of the noble metal nanoparticles.

2. The noble metal nanomedicine of claim 1, wherein the mixture is substantially free of non-catechin flavonoids.

3. The noble metal nanomedicine of claim 1, wherein the mixture is substantially free of non-(+)-catechin (2R,3S) catechins.

4. The noble metal nanomedicine of claim 1, wherein the mixture is present in an amount of 1 to 50 wt %, based on a total weight of noble metal nanomedicine.

* * * * *